United States Patent [19]
Goldowsky

[11] Patent Number: 6,068,588
[45] Date of Patent: May 30, 2000

[54] COUNTERBALANCED PUMP

[75] Inventor: Michael Philip Goldowsky, Valhalla, N.Y.

[73] Assignee: International Business Machines Corporation, Armonk, N.Y.

[21] Appl. No.: 09/227,107

[22] Filed: Jan. 7, 1999

[51] Int. Cl.[7] .................................................. A61M 1/12
[52] U.S. Cl. .............................................................. 600/16
[58] Field of Search ........................................ 600/16, 17

[56] References Cited

U.S. PATENT DOCUMENTS 4,389,849  6/1983  Gasser et al. .

OTHER PUBLICATIONS

Stolfi et al, "A Magnetically Suspended Linearly Driven Cryogenic Refrigerator," NASA Report N84–15345, Dec. 1983, pp: 263–303.

Teague, "Robert Jarvik: Courage to Test Medicine's Frontier," Design News, Jul. 11, 1994, pp: 60 & 61.

*Primary Examiner*—William E. Kamm
*Attorney, Agent, or Firm*—Francis L. Conte

[57] ABSTRACT

Fluid is periodically pumped through a motor-driven tubular pump at a substantially constant pumping frequency. The pump includes at least one resiliently reciprocate counterbalancing ring joined to a cooperating spring having a fundamental natural frequency corresponding with the pumping frequency and pumping flowrate is varied independently of the pumping frequency.

22 Claims, 3 Drawing Sheets

COUNTERBALANCED PUMP

BACKGROUND OF THE INVENTION

The present invention relates generally to fluid pumps, and, more specifically, to a pump configured for pumping blood in a living body.

The present invention is an improvement over the linear pump described in U.S. patent application Ser. No. 08/686,618; filed Jul. 19, 1996 now Pat. No. 5,924,975, and assigned to the present assignee. This type of linear pump includes a tubular piston mounted in a tubular housing for reciprocation therein. First and second check valves are joined to the housing and piston, respectively, for controlling fluid flow through the respective bores thereof for unidirectional flow. A linear motor is operatively joined between the piston and housing for periodically reciprocating the piston for in turn periodically pumping the fluid in unidirectional, pulsatile flow.

When used for pumping blood in a living body, the pump is surgically implanted near the heart for receiving blood from the left atrium and pumping it to the aorta as a left ventricular assist device (LVAD). A particular advantage of this linear pump is the hydrodynamic suspension of the piston within the housing using the pumping fluid or blood as a bearing fluid. The outer surface of the piston is spaced radially inwardly from the inner surface of the housing bore and is configured as either a linear or rotary hydrodynamic bearing for suspending the piston during reciprocation thereof, with minimum or no damage to the blood flowing therethrough.

Since the flowrate requirements of a natural heart vary for physiological reasons, the blood pump must be operated to correspondingly change the pumping flowrate therethrough. This is typically accomplished by varying the reciprocation frequency of the piston while utilizing the full stroke capability thereof. However, during operation the reciprocating piston causes corresponding vibration and movement of the pump which are undesirable when excessive.

Accordingly it is desired to reduce or eliminate vibration and movement of a blood pump implantable in a patient.

BRIEF SUMMARY OF THE INVENTION

Fluid is periodically pumped through a tubular pump at a substantially constant pumping frequency. The pump includes a counterbalancing ring joined to a cooperating spring having a fundamental natural frequency corresponding with the pumping frequency. And, pumping flowrate is varied independently of the pumping frequency.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
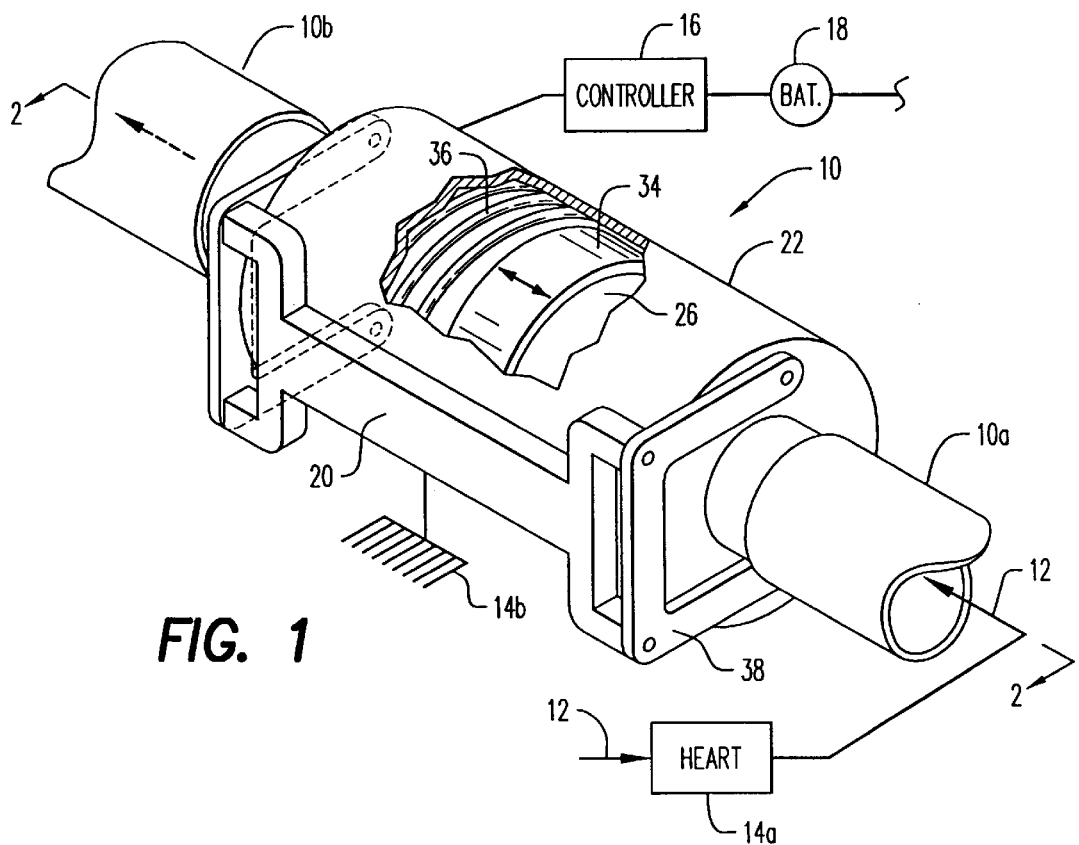
FIG. 1 is an isometric schematic view of a linear pump implantable in a chest cavity adjacent a heart, and counterbalanced in accordance with an exemplary embodiment of the present invention.

Illustrated in FIG. 1 is a linear pump 10 configured for being implanted in a human chest cavity for pumping fluid or blood 12 in accordance with an exemplary embodiment of the present invention. In this example, the pump is configured as a left ventricular assist device (LVAD) surgically attached between the left atrium and descending aorta of a human heart 14a. The pump includes a suitable inlet tube 10a sutured to an opening in the left atrium and a suitable outlet tube 10b sutured to the descending aorta.

The pump is controlled by an electrical controller 16 electrically joined thereto, and is powered by an implanted battery 18 electrically joined to the controller. The pump, controller, and battery are implanted in the body below the skin, and the battery may be periodically charged by a conventional induction charging device cooperating with an external induction coil outside the body in a known configuration. The basic linear pump may be like that described in the above identified patent application, incorporated herein by reference. However, it may be further improved in accordance with the present invention as herein described.

In the exemplary embodiment illustrated in FIG. 1, the pump includes a rigid frame 20 for fixedly attaching the pump inside the body to the rib cage 14b for example. The frame is described in more detail hereinbelow.

Figure 2:
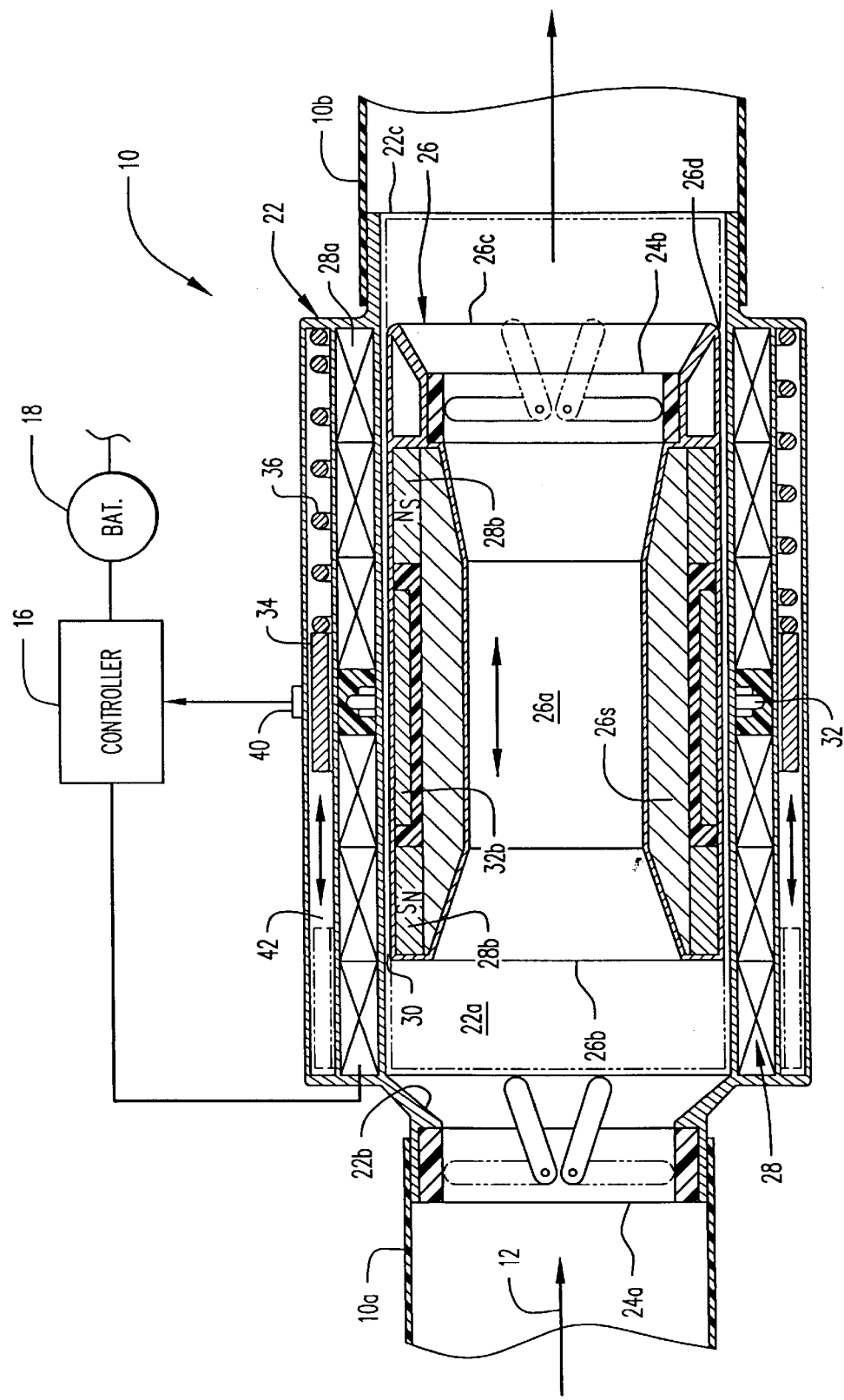
FIG. 2 is an axial sectional view through the linear pump illustrated in FIG. 1 and taken along line 2—2.

As shown in FIG. 2, the pump 10 is preferably tubular and includes a tubular, hollow housing 22 having a coaxial, smooth cylindrical center bore 22a disposed in flow communication between a pump or housing inlet 22b and a pump or housing outlet 22c axially spaced apart from each other at opposite ends of the housing. A first, one-way or check valve 24a is fixedly joined in the housing inlet for controlling flow of the blood through the housing bore. In an alternate embodiment, the first valve may instead be located in the housing outlet.

A tubular or cylindrical piston 26 is disposed coaxially in the housing bore for axial translation therein. The piston is hollow and includes a coaxial smooth center bore 26a disposed in flow communication between a piston inlet 26b and a piston outlet 26c axially spaced apart from each other at opposite ends of the piston. A second, one-way or check valve 24b is fixedly joined in the piston outlet for controlling flow of the blood through the piston bore. In an alternate embodiment, the second valve may instead be installed in the piston inlet.

In this configuration, the respective inlets, bores, and outlets of the housing and piston are disposed in serial flow communication for channeling the blood therethrough in turn as it is pumped through the pump, and bathing the entire piston in blood.

A linear motor 28 includes a plurality of axially adjoining, coaxial stator drive coils 28a disposed in the housing, which cooperate with a pair of axially spaced apart permanent magnet rings 28b disposed in the piston. The magnet rings are also spaced radially inwardly of the drive coils for magnetically cooperating therewith to axially translate or oscillate the piston in reciprocation in the housing for cyclically pumping the blood in turn through the housing and piston inlets 22b,26b and outlets 26c,22c in unidirectional flow through the housing and piston bores 22a,26a.

Since the pump is specifically configured in the exemplary embodiment for pumping blood in a living body, the housing and piston are preferably encapsulated in a suitable biocompatible material for being implanted into the body and pumping blood through the housing and piston bores. This is accomplished in one example by forming the outer surfaces of the housing and piston in the form of thin titanium shells or cans, which themselves may be suitably coated with a biocompatible material such as carbon if desired.

The piston illustrated in FIG. 2 includes a cylindrical outer surface or journal 26d which is predeterminedly spaced radially inwardly from the housing bore to define a hydrodynamic bearing therewith having a radial gap 30 for receiving a portion of the blood from the housing bore as a bearing fluid for hydrodynamically supporting the oscillatory piston in the housing. The housing inner surface, defining the bore, is suitably smooth, and the complementary piston journal is also in most parts smooth. The piston gap 30 is nominally a circular annulus which extends completely between the opposite axial ends of the piston in flow communication with the housing bore.

The piston journal 26d may be configured to the define a linear hydrodynamic bearing, or a rotary hydrodynamic bearing, or both, in which the blood develops a pressure force during movement of the piston to suspend the piston radially inwardly from the housing bore on a film of blood in a low friction arrangement. The blood provides the bearing fluid preventing contact of the piston with the housing bore which reduces or eliminates damage to the blood as it is pumped.

Accordingly, the piston 26 is entirely bathed in blood and provides pumping action through its bore 26a. And, the flow of the blood in the piston gap effects a hydrodynamic bearing for suspending the piston away from the housing bore for providing substantially frictionless movement thereof.

In operation, the linear motor is powered and controlled by the controller 16 for magnetically axially translating the piston in the housing bore in a forward or eject stroke followed in turn by an aft or reset stroke. The piston therefore axially reciprocates forward and aft to linearly pump the blood along the axial centerline axis of the pump in a unidirectional forward flow from the housing inlet to the housing outlet. The one-way check valves cooperate with the reciprocating piston for obtaining the unidirectional flow.

In FIG. 2, the piston is illustrated in solid line in the middle of its forward eject stroke, with the first valve 24a being open and the second valve 24b being closed for blocking reverse flow through the piston bore. In this way, the piston provides a forward moving plug which pushes the blood forwardly and outwardly through the housing outlet. At the same time, additional blood enters the housing inlet.

In the aft reset stroke, the piston moves rearwardly which causes the second valve 24b to open, as shown in phantom line, with the first valve 24a being closed, as also shown in phantom line. The closed first valve restrains reverse blood flow, while the open second valve allows the piston to reset, without flow obstruction, to the beginning of its travel for the next cycle. In this way, the linear pump is effective for pumping the blood in periodic pulses in pulsatile flow in only the forward direction.

Hydrodynamic bearing forces may be developed solely by the axial movement of the piston in the housing, or the piston may be rotated for circumferentially developing hydrodynamic pressure in the bearing fluid, with the bearing defining a journal bearing. In this case, spinning of the piston may be effected in any suitable manner such as by introducing either a rotary motor specifically configured therefor, or introducing impeller vanes in the piston which turn the piston as the blood is pumped.

In the exemplary embodiment illustrated in FIG. 2, two groups of three drive coils 28a are coaxially aligned inside the housing 22 concentrically around the housing bore. A position sensor 32 is disposed at the middle of the drive coils and is operatively joined to the controller. The sensor 32 detects grooves machined into the outer diameter of an iron sleeve 32b located beneath the titanium can of the piston. By counting pulses due to travel of the sleeve, the piston position can be determined. The position sensor thusly allows the individual coils to be switched on and off in sequence as the piston moves in the manner of a voice coil linear motor. This commutation technique may be used to accurately vary the stroke of the piston.

The tubular linear pump 10 illustrated in FIGS. 1 and 2 provides substantial advantages when used for pumping blood since it simply uses the single moving piston bathed and suspended in the blood. The cooperating valves ensure unidirectional blood flow, which is periodic and corresponds with the reciprocation of the piston. However, such piston reciprocation introduces shaking or vibratory forces in the pump which may be undesirable if excessive.

For example, although the pump periodically pumps the blood therethrough, a nominal or average flowrate having a positive value is effected which introduces a corresponding nominal force in the pump which must be restrained by its mounting frame 20. Since the piston reciprocates in eject and reset strokes, it is subject to diastolic and systolic pressure forces acting thereon which occur over a half cycle, i.e., the eject stroke. Furthermore, the piston is necessarily accelerated and decelerated for reciprocation and is subject to inertia forces thereon. And, the blood being pumped itself introduces a fluid inductance.

These several factors are combined together during operation and result in a combined periodic force acting on the pump housing which in turn is carried through the frame 20 to the supporting rib cage 14b for example. The resulting shaking force from the reciprocating pump varies according to the size of the pump and the corresponding flowrate therethrough. For a typical LVAD application, the shaking forces from the reciprocating pump may be undesirably high, thus limiting the suitability of the pump.

In accordance with the present invention, the basic linear pump may be improved by periodically pumping the fluid through the pump at a substantially constant pumping frequency, and a corresponding reciprocation frequency, and additionally counterbalancing the pumping force in the pump at a fundamental natural frequency corresponding with the pumping frequency.

In the exemplary embodiment illustrated in FIGS. 1 and 2, counterbalancing is effected by resiliently reciprocating a counterbalancing ring 34 around the housing 22 at the fundamental natural frequency. The ring 34 is loosely disposed coaxially around the housing 22 and hermetically sealed therein for axial reciprocation. A coil spring 36 is fixedly joined at opposite ends thereof to the ring 34 and the housing 22, by welding or other suitable bonding. And, the ring and spring are sized in mass and spring rate, respectively, to effect the desired fundamental natural frequency.

As shown in FIG. 1, means in the exemplary form of leaf springs 38 are disposed at opposite ends of the frame 20 for resiliently supporting the housing 22 on the frame which cooperate with the coil spring 36 for counterbalancing the pump during operation.

Figure 3:
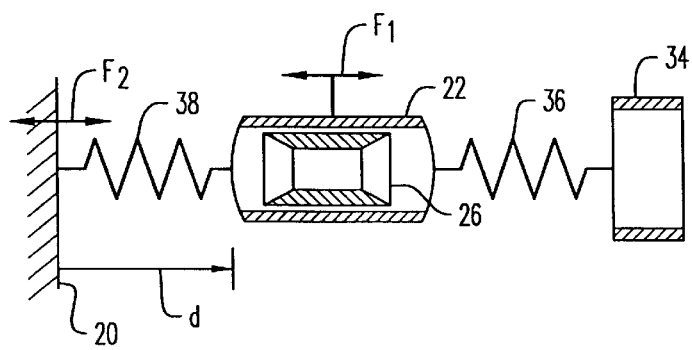
FIG. 3 is a schematic representation of the linear pump illustrated in FIG. 1 with a reciprocating piston and counterbalance ring resiliently supported in a tuned system for counterbalancing pumping force during operation.

FIG. 3 is a schematic representation of the pump including the counterbalance ring 34 attached to the housing 22 by the coil spring 36, with the collective assembly being attached to the stationary frame 20 by the leaf springs 38. The various forces created during pumping are designated $F_1$ and act on the housing 22 as axial shaking forces. Those forces are carried through the leaf springs 38 to the frame 20 which experiences resulting shaking forces designated $F_2$.

Since the invention is practiced by operating the piston 26 at a substantially constant reciprocating frequency, the resulting shaking forces $F_1$ may be represented in a conventional Fourier series. The Fourier series includes a constant component of the shaking force and additional components associated with the fundamental reciprocation or pumping frequency and higher order harmonics thereof. For example, the piston 26 may be operated at a constant frequency of about 9 Hertz (Hz) and sized with maximum flow volume for achieving the desired maximum flowrate in a typical application.

In the Fourier series representation of the shaking forces $F_1$, a relatively large force is associated with the fundamental pumping frequency at 9 Hz, with correspondingly decreasing values of forces associated with the higher order harmonics at 18, 27, and 36 Hz, etc., which are typically relatively small in magnitude and generally negligible.

Based on the schematic of FIG. 3, a transfer function may be conventionally derived representing the force transfer from the housing 22 to the frame 20, and is represented by the following equation:

$$\frac{F_2}{F_1} = \frac{k_1/k_2(1-(w/w_2)^2)}{(1-(w/w_2)^2)(-(m_1/m_2)(w/w_2)^2 + k_1/k_2 + 1) - 1} \quad (1)$$

In equation 1, $k_1$ represents the spring rate for the leaf springs 38; $k_2$ represents the spring rate for the coil spring 36; w is the pumping frequency or reciprocation frequency of the piston measured in radians per second, and $w_2$ is the fundamental natural frequency of the counterbalance ring 34 and its supporting spring 36 as represented by the square root of the quotient of spring rate of the spring 36 and mass of the ring 34.

By matching the pumping frequency of the pump and the fundamental natural frequency of the counterbalance ring, the frequency ratios ($w/w_2$) in equation 1 are equal to 1, causing the transfer function to have a zero value. In this way, the Fourier series force component for the fundamental natural frequency will be zero when the pumping frequency matches the natural frequency of the suspended counterbalance ring 34. Although the higher order harmonic components of the Fourier series force are not zero in value, they are nevertheless substantially reduced in magnitude, by at least an order of magnitude for example.

Furthermore, the axial displacement d of the housing 22 relative to its frame 20 is illustrated in FIG. 3 and has a zero value for the fundamental frequency component of the vibratory motion. And, this displacement has substantially small values for the higher order harmonic vibration components decreasing in turn.

Accordingly, by introducing the counterbalance ring 34 and its support spring 36 with a fundamental natural frequency tuned to the pumping frequency of the pump, a significant portion of the vibratory motion of the pump is eliminated, with higher order harmonic motion being substantially reduced.

Furthermore, equation 1 indicates that the ratio of the spring rates ($k_1/k_2$) for the two springs 36,38 affects the force transfer function, and in turn affects the housing displacement d. However, analysis indicates that whether the leaf springs 38 are relatively soft or relatively stiff in spring rate, substantial force attenuation is nevertheless obtained for the higher order harmonic vibratory components, with the fundamental vibratory component having a zero value.

In one exemplary embodiment analyzed, the pump 1 0 illustrated in FIG. 2 has an outer diameter of about 5 cm and a main housing length of about 9 cm, with the piston being operated at 9 Hz for producing a maximum flowrate of about 8 liters/minute.

An exemplary counterbalance ring 34 is sized in diameter to fit just within the outer diameter of the housing and has a thickness of about 2.3 mm and a length of about 18 mm and a mass of about 113 grams. The coil spring 36 may have a spring rate of about 40 g/mm with the leaf springs 38 collectively having a spring rate of about 100 g/mm.

Accordingly, by providing the counterbalance ring 34 and its suspension spring 36 around the housing 22, the pump may be operated at a substantially constant frequency matching the fundamental natural frequency of the suspended counterbalance ring 34 for substantially eliminating the fundamental mode of vibration, including the axial force component and motion associated therewith. And, the force and motion of the higher order harmonic components are also substantially reduced, which in turn reduce the shaking force and motion on the frame 20 and the inlet and outlet tubes 10a,b.

However, the pump should nevertheless have the capability to vary flowrate as required in assisting the heart. This may be accomplished in accordance with another feature of the present invention by varying the pumping flowrate through the pump independently of the pumping frequency which must remain tuned to the natural frequency of the suspended ring 34.

Pumping flowrate may be varied by varying the axial stroke of the piston 26 inside the housing 22. This may be effected by configuring the controller 16 for both controlling the reciprocation frequency of the piston to a substantially constant value, and varying the stroke of the piston in the housing bore which is independent of the pumping frequency. The several adjoining coils 28a and position sensor 32 illustrated in FIG. 2 allow control of the stroke of the piston from a minimum value to a maximum value within the available axial space of the housing. Maximum pumping flowrate is obtained with maximum stroke of the piston, and minimum flowrate is obtained with minimum stroke.

In the preferred embodiment in FIG. 2, another sensor in the exemplary form of an accelerometer 40 is fixedly mounted to the housing 22 for measuring axial acceleration of the housing as the blood is periodically pumped therethrough. The controller 16 is joined in a feedback closed-loop with the accelerometer 40 and motor 28 for automatically adjusting the pumping frequency to substantially match the fundamental natural frequency of the suspended counterbalance ring in response to the measured acceleration as it is driven toward zero. In this way, the counterbalanced pump may be optimized in operation to precisely match the pumping frequency to the fundamental natural frequency thereof to minimize the axial vibratory force and motion.

A particular advantage of the present invention is the introduction of the counterbalance ring 34 in a compact arrangement with a relatively small pump 10 permitting unobstructed flow of the blood along the centerline axis of the pump. Whereas the blood is pumped through the respective bores of the housing and piston, the counterbalancing is performed outside the bores and inside the hermetically sealed housing 22 in a compact arrangement.

As initially shown in FIG. 2, the housing includes an annular slot 42 disposed coaxially therearound within the outer wall thereof for concentrically receiving the counterbalance ring 34. In the preferred embodiment, a single coil spring 36 is also disposed at one end of the slot on one side of the ring, with the slot on the opposite side of the ring being empty for permitting unobstructed axial travel of the ring therein. The ring 34 is suitably attached to one end of the spring, either mechanically or by brazing for example, with the opposite end of the spring being suitably attached to the end wall of the housing. In this way, the ring is free to oscillate axially within the available axial extent of the slot 42 for counterbalancing the axial vibratory motion of the pump during operation.

The use of the single coil spring 36 ensures a precise fundamental natural frequency of the suspended ring 34 as it oscillates within the slot 42. The slot 42 extends the full axial length of the main housing to maximize the counterbalancing forces from the ring 34 within the limited available space. The ring 34 is preferably made of a high density metal such as tungsten for minimizing its volume, although alternative metals such as dense uranium may also be used.

Figure 4:
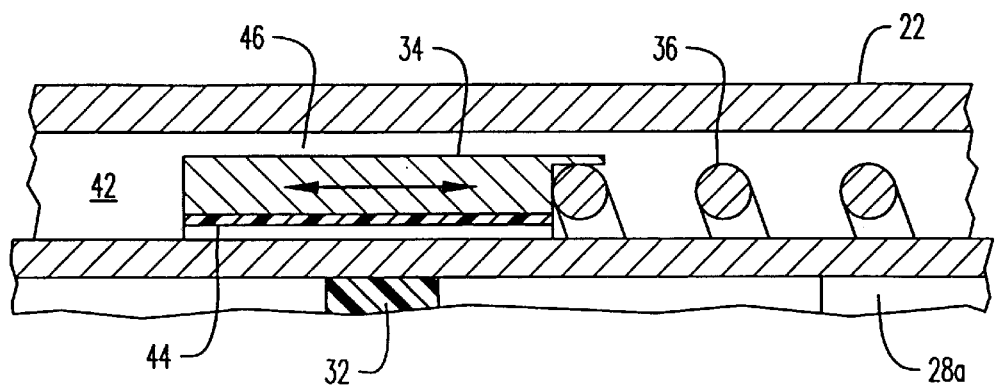
FIG. 4 is an enlarged axial sectional view through a portion of the counterbalance ring and adjoining spring within a portion of the housing illustrated in FIG. 2.

Since the counterbalance ring 34 oscillates during operation, it is preferably mounted for substantially frictionless travel. As shown in FIG. 4, the ring 34 may include a lubricant coating 44, such as Delrin plastic or polytetrafluoroethylene (PTFE), around either its inner or outer perimeter thereof. For example the inner diameter of the ring is sized and coated to closely match the outer diameter of a sleeve surrounding the drive coils for sliding therealong with low friction.

The ring is preferably spaced radially inwardly from the inner surface of the housing outer wall to define a radial gap 46 sized, 0.13 mm for example, to permit substantially unobstructed gas flow therethrough as the ring reciprocates in the slot 42. The housing 22 is a hermetically sealed enclosure trapping ambient air within the slot 42. As the ring reciprocates in the slot, the gap 46 permits the air contained therein to flow past the ring for permitting its free resonant oscillation.

A significant advantage of the present invention is that the original linear pump may remain substantially identical in configuration and size while integrating therein the counterbalance ring and its suspension spring. In a preferred embodiment, the outer diameter of the housing 22 may remain unchanged upon the addition of the counterbalance ring 34, with the space required therefor being obtained by slightly reducing the diameter of the piston 26 and the cooperating drive coils 28a.

Since the counterbalance ring 34 is preferably disposed near the outer diameter of the housing, it utilizes that outer diameter to minimize its radial thickness for obtaining a suitable mass in the available space. The slot 42 preferably extends the maximum available axial length corresponding with that of the drive coils 28a for minimizing the ring mass. Accordingly, the ring can oscillate with full axial travel within the available space of the slot 42, which minimizes the amount of mass for a desired counterbalancing force.

If desired, the counterbalance ring could also be mounted around either the housing inlet or outlet 22b,c, with suitable axial extensions thereof if desired. Counterbalance rings may be used at any one or more of these three locations.

Since a single counterbalance ring may be used for counterbalancing a single vibratory frequency, two or more counterbalance rings and cooperating springs may be used for fully counterbalancing two corresponding vibratory frequencies, such as the fundamental frequency and the first harmonic thereof.

Two different fundamental pumping frequencies may also be used and counterbalanced, including a high flowrate range using a high pumping frequency, and a relatively low flowrate range using a low pumping frequency. The advantage in employing a two-frequency pump when pumping blood is greater flow pulsatility in the lower flowrate range varied by axial stroke.

The majority of patient need is up to about 5 liters per minute (L/m), for example, and this can be achieved using the maximum piston stroke at a low frequency such as 6 Hertz (Hz). This gives high pulsatility due to the larger stroke. When flows greater than 5 L/m are required, the pump is operated at its high range setting, such at 9.6 Hz, to obtain up to 8 L/m at full stroke. The use of two tuned countermasses can completely balance the corresponding fundamentals at both frequency settings.

Figure 5:
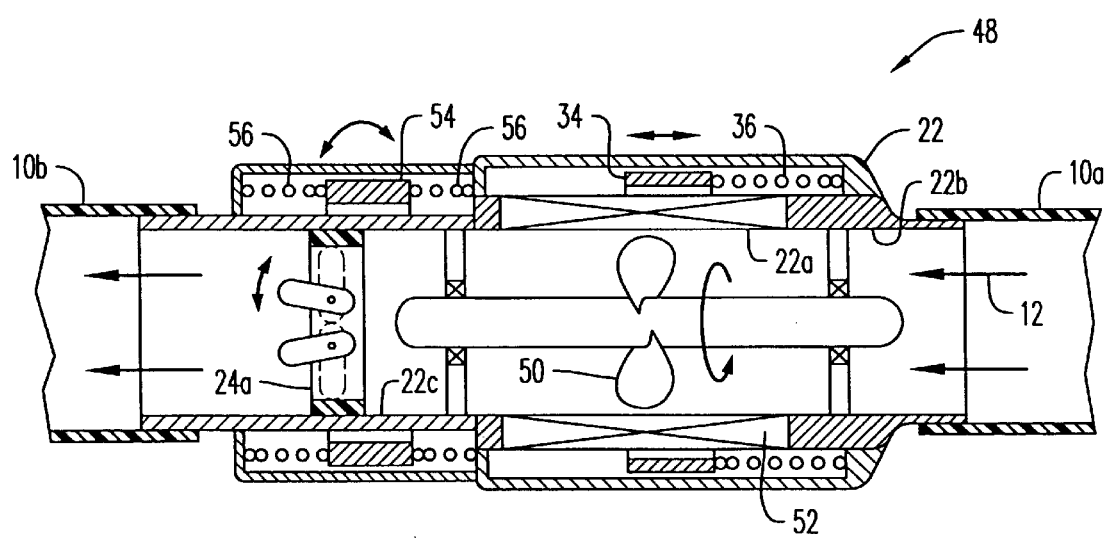
FIG. 5 is an axial sectional view of a linear axial flow pump having a rotary impeller therein and a pair of counterbalancing rings for axial and torsional counterbalancing in accordance with another embodiment of the present invention.

Although the invention may be used for the linear pump 10 having an axially reciprocating piston, it may also be used for other types of linear or axial flow pumps such as the FIG. 5 pump 48 having a rotary impeller 50 disposed coaxially in the housing bore 22a. In this embodiment, the impeller 50 is mounted on a shaft supported in suitable bearings at opposite ends of the shaft mounted to stationary radial struts extending across the housing bore.

A rotary motor 52 is operatively joined to the impeller 50 for periodic rotation thereof at a substantially constant pumping frequency. In one embodiment, the motor 52 includes drive coils mounted in the housing 22, with cooperating permanent magnets mounted in the radial tips of the impeller 50 for rotating the impeller during operation to pump the blood 12.

Although the impeller 50 may be operated continuously for continuously pumping blood through the pump, it may be desirable to include a check valve in the housing, such as the first check valve 24a, and operate the pump periodically so that the check valve may open and close for producing pulsatile flow corresponding with a natural heart pulsatile flow, but at a different frequency. The valve prevents backflow of blood through the pump and maintains its ability to open and close by repeated cycling, which is desirable to prevent backflow therethrough in the event of a pump failure.

The rotary motor 52 is therefore preferably cycled at higher and lower rotary speeds in the same direction to create pulsatile blood flow for correspondingly opening and closing the check valve 24a. The cycling pump is subject to rotary vibration in the circumferential direction with corresponding vibratory forces and motion. This torsional vibration may be reduced in accordance with another embodiment of the present invention as illustrated in FIG. 5.

More specifically, by varying the pumping speed sinusoidally at a predetermined constant frequency a torsional counterbalance ring 54 and cooperating torsion spring 56 may be used for counterbalancing the fundamental torsional frequency vibration. In this embodiment, two of the torsion springs are joined on opposite sides of the ring 54 and collectively provide a common spring rate therefor.

The torsion springs allow the ring 54 to circumferentially oscillate, for torsion counterbalancing. The periodic rotating frequency of the impeller 50 may be held constant to match the fundamental torsional natural frequency of the suspended torsion ring 54 for substantially reducing or eliminating the corresponding torsional vibration forces and movement.

Furthermore, since the rotary pump illustrated in FIG. 5 also effects axial pulses of blood flow, the pump is also subject to axial vibration, which again may be reduced by additionally incorporating the axially translating counterbalance ring 34 and its suspension spring 36 in a manner similar to the first embodiment disclosed above.

Since two counterbalance rings and springs may be disposed in the housing, the pump may be counterbalanced at two corresponding natural frequencies. These two frequencies may correspond with axial and torsional vibratory modes, or with two axial modes if desired. In this latter case, the pump may be operated at two different pumping frequencies as disclosed above, and effectively counterbalanced thereat by the correspondingly tuned different rings and springs.

In both embodiments disclosed above, a relatively thin counterbalance ring 34,54 may be used with a cooperating suspension spring 36,56 at the outer diameters of the respective pumps for providing effective counterbalancing thereof for axial and torsional vibration in substantially compact and robust configurations. The counterbalance rings are fully contained within the respective housings without substantial changes in configuration or size of the respective pumps. And, the counterbalanced pumps work effectively with various forms of suspensions, such as the frame 20 and leaf springs 38 illustrated in FIG. 1. The suspension of the pump itself in the body cavity is secondary to the integrated counterbalancing rings therein. The pumps may be supported in the body over a range from soft to stiff while still maintaining effective counterbalancing performance during pulsatile blood flow.

Accordingly, what is desired to be secured by Letters Patent of the United States is the invention as defined and differentiated in the following claims in which I claim:

1. A method of pumping a fluid through a tubular pump comprising:
   periodically pumping said fluid through said pump at a substantially constant pumping frequency;
   counterbalancing pumping force in said pump at a fundamental natural frequency corresponding with said pumping frequency; and
   varying said flowrate of said fluid through said pump independently of said pumping frequency.

2. A method according to claim 1 wherein:
   said pump includes a tubular housing having an inlet, bore, and outlet in serial flow communication for channeling said fluid therethrough;
   said fluid is pumped through said bore; and
   said counterbalancing is performed outside said bore and inside said housing.

3. A method according to claim 2 wherein:
   said fluid is periodically pumped through said housing bore using a reciprocating hollow piston therein having a check valve for effecting unidirectional flow; and
   said flowrate is varied by varying stroke of said piston.

4. A method according to claim 3 wherein said counterbalancing is effected by resiliently reciprocating a counterbalancing ring around said housing at said fundamental natural frequency.

5. A method according to claim 2 wherein said counterbalancing is effected by resiliently reciprocating a counterbalancing ring around said housing at said fundamental natural frequency.

6. A method according to claim 5 wherein said ring is axially reciprocated.

7. A method according to claim 5 wherein said ring is circumferentially reciprocated.

8. A method according to claim 2 further comprising:
   measuring acceleration of said housing as said fluid is periodically pumped therethrough; and
   adjusting said pumping frequency to substantially match said fundamental natural frequency in response to said measured acceleration.

9. A method according to claim 2 wherein said fluid is blood, and said pump is resiliently mounted inside a human chest cavity for pumping said blood in heart assist.

10. A pump for pumping a fluid comprising:
   a tubular housing having an inlet, bore, and outlet in serial flow communication for channeling said fluid therethrough;
   means disposed at least in part inside said bore for periodically pumping said fluid through said pump at a substantially constant pumping frequency;
   means for counterbalancing pumping force in said pump at a fundamental natural frequency corresponding with said pumping frequency; and
   means for varying flowrate of said fluid through said pump independently of said pumping frequency.

11. A pump according to claim 10 wherein said pumping means comprise:
   a piston disposed coaxially in said housing bore, and having an inlet, bore, and outlet in serial flow communication, and a check valve fixedly joined thereto; and
   a motor disposed in part in said housing and in part in said piston to reciprocate said piston in said housing bore at said pumping frequency to pump said fluid in turn through said housing and piston inlets and outlets in unidirectional flow through said housing and piston bores.

12. A pump according to claim 11 wherein said counterbalancing means comprise:
   a ring disposed coaxially around said housing;
   a spring fixedly joined at opposite ends to said ring and housing; and
   said ring and spring are sized in mass and spring rate to effect said fundamental natural frequency.

13. A pump according to claim 12 wherein said housing includes an annular slot receiving said ring and a single one of said spring at one end of said ring, with an opposite end of said ring having unobstructed travel in said slot.

14. A pump according to claim 13 further comprising a controller operatively joined to said motor for controlling said pumping frequency, and configured for varying stroke of said piston in said housing bore for varying flowrate of said fluid through said pump independently of said pumping frequency.

15. A pump according to claim 14 further comprising:
   an accelerometer mounted to said housing for measuring acceleration of said housing as said fluid is periodically pumped therethrough; and
   said controller is joined in a feedback closed-loop with said accelerometer and motor for adjusting said pumping frequency to substantially match said fundamental natural frequency in response to said measured acceleration.

16. A pump for pumping a fluid comprising:

a tubular housing having an inlet, bore, and outlet in serial flow communication for channeling fluid therethrough;

a tubular piston disposed coaxially in said housing bore, and having an inlet, bore and outlet;

a motor operatively joined between said housing and piston to reciprocate said piston in said housing bore to effect a substantially constant pumping frequency; and a counterbalancing ring loosely disposed inside said housing and fixedly joined to one end of a spring having an opposite end fixedly joined to said housing, and said ring and spring are sized to effect a fundamental natural frequency substantially equal to said pumping frequency.

17. A pump according to claim 16 further comprising:

a first check valve joined to said housing; and a second check valve joined to said piston for controlling flow of said fluid unidirectionally through said housing and piston upon reciprocation of said piston.

18. A pump according to claim 17 wherein said housing further comprises an annular slot receiving said ring and spring, with said spring being disposed solely on one end of said ring, with an opposite end of said ring having unobstructed travel in said slot.

19. A pump according to claim 18 wherein said ring includes a lubricant coating around a perimeter thereof, and is spaced radially from said housing to define a radial gap sized to permit substantially unobstructed gas flow therethrough as said ring reciprocates in said slot.

20. A pump according to claim 17 further comprising:

a frame disposed adjacent said housing; and means for resiliently supporting said housing on said frame for further counterbalancing said pump.

21. A pump according to claim 17 further comprising two of said counterbalancing rings and corresponding springs disposed in said housing and sized to effect two different natural frequencies for operating said pump at two different pumping frequencies corresponding thereto.

22. A pump for pumping a fluid comprising:

a tubular housing having an inlet, bore and outlet in serial flow communication;

a rotary impeller disposed coaxially in said housing bore;

a motor operatively joined to said impeller for periodic rotation thereof at a substantially constant pumping frequency; and a counterbalancing ring loosely disposed inside said housing and fixedly joined to one end of a torsion spring having an opposite end fixedly joined to said housing, and said ring and spring are sized to effect a fundamental natural frequency substantially equal to said pumping frequency.

* * * * *